(12) United States Patent
Anand

(10) Patent No.: US 10,585,083 B2
(45) Date of Patent: Mar. 10, 2020

(54) SYSTEM AND METHOD FOR PREDICTING VISCOSITY OF HEAVY OIL FORMATIONS BASED ON NUCLEAR MAGNETIC RESONANCE (NMR) MEASUREMENTS

(71) Applicant: Schlumberger Technology Corporation, Sugar Land, TX (US)

(72) Inventor: Vivek Anand, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 465 days.

(21) Appl. No.: 15/180,246

(22) Filed: Jun. 13, 2016

(65) Prior Publication Data

US 2017/0356896 A1  Dec. 14, 2017

(51) Int. Cl.
| | |
|---|---|
| *G01N 33/28* | (2006.01) |
| *G01V 3/32* | (2006.01) |
| *G01N 11/00* | (2006.01) |
| *G01R 33/44* | (2006.01) |
| *E21B 47/00* | (2012.01) |
| *G01N 24/08* | (2006.01) |

(52) U.S. Cl.
CPC ......... *G01N 33/2823* (2013.01); *E21B 47/00* (2013.01); *G01N 11/00* (2013.01); *G01N 24/081* (2013.01); *G01R 33/448* (2013.01); *G01V 3/32* (2013.01); *Y02A 90/344* (2018.01)

(58) Field of Classification Search
USPC ...................................................... 324/303
See application file for complete search history.

(56) References Cited

U.S. PATENT DOCUMENTS

| | | | | |
|---|---|---|---|---|
| 9,507,047 | B1* | 11/2016 | Dvorkin | G01V 5/101 |
| 2002/0167314 | A1* | 11/2002 | Prammer | G01N 24/081 |
| | | | | 324/303 |
| 2004/0008027 | A1* | 1/2004 | Prammer | G01N 24/081 |
| | | | | 324/303 |
| 2005/0270023 | A1* | 12/2005 | Freedman | G01V 3/32 |
| | | | | 324/303 |

(Continued)

FOREIGN PATENT DOCUMENTS

WO  2017074712 A2  5/2017

OTHER PUBLICATIONS

Alboudwarej et al., "Highlighting Heavy Oil", Oilfield Review, vol. 18, No. 2, 2006, pp. 34-53.

(Continued)

*Primary Examiner* — Jay Patidar
(74) *Attorney, Agent, or Firm* — Trevor G. Grove

(57) ABSTRACT

This disclosure describes systems and methods to predict viscosity of heavy oil in a geological formation, even when the geological formation also contains water such as clay-bound water, using a downhole nuclear magnetic resonance (NMR) tool. The downhole NMR tools may obtain responses include distributions of a first relaxation time T1, a second relaxation time T2, or diffusion, or a combination of these. The responses of the NMR measurements that are due to water are separated from the responses of the NMR measurements that are due to heavy oil. The responses of the NMR measurements due to heavy oil are then related to likely values of viscosity of the heavy oil based on empirical or simulated measurements.

15 Claims, 5 Drawing Sheets

(56) References Cited

U.S. PATENT DOCUMENTS

| | | | | |
|---|---|---|---|---|
| 2008/0204013 A1* | 8/2008 | Badry | .................. | G01N 24/081 324/303 |
| 2010/0109664 A1* | 5/2010 | Minh | ....................... | G01V 3/32 324/303 |
| 2010/0271019 A1* | 10/2010 | Anand | ................. | G01N 24/081 324/303 |
| 2010/0313633 A1* | 12/2010 | Anand | ................... | G01N 24/08 73/38 |

OTHER PUBLICATIONS

Curtis et al., "Heavy Oil Reservoirs", Oilfield Review, vol. 14, No. 3, 2002, pp. 30-51.

Morriss et al., "Hydrocarbon Saturation and Viscosity Estimation from NMR Logging in the Belridge Diatomite", Society of Petrophysicists and Well Log Analysts 35th Annual Symposium, Jun. 19-22, 1994, 24 pages.

Lo et al., "Relaxation Time and Diffusion Measurements of Methane and n-Decane Mixtures", The Log Analyst, Nov.-Dec. 1998, pp. 43-47.

* cited by examiner

SYSTEM AND METHOD FOR PREDICTING VISCOSITY OF HEAVY OIL FORMATIONS BASED ON NUCLEAR MAGNETIC RESONANCE (NMR) MEASUREMENTS

BACKGROUND

This disclosure relates to predicting viscosity in heavy oil formations and, more particularly, to predicting viscosity in heavy oil formations that include water such as clay-bound water.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Heavy oil constitutes a large quantity of the total oil resources of the world. The abundance of heavy oil resources, decline in the production of conventional oil reservoirs, and high oil prices have led to a renewed interest in producing heavy oil. The viscosity of heavy oils may vary substantially. The American Petroleum Institute defines gravities of heavy oils to cover a wide range, from 22 for light heavy oils to 10 for extraheavy oils. Accurately characterizing heavy oil properties, such as viscosity, allows operators to determine optimal recovery techniques and to predict production rates and recoverable oil volumes.

Some downhole tools that can be used to predict the viscosity of oil collect measurements of nuclear magnetic resonance (NMR) in a wellbore through a geological formation of interest. Downhole NMR tools may measure the response of nuclear spins in formation fluids to applied magnetic fields. The measurements obtained by downhole NMR tools may include distributions of a first relaxation time T1, a second relaxation time T2, or diffusion, or a combination of these. For example, a downhole NMR tool may measure just T2 distribution, or the tool may measure a joint T1-T2 distribution or T1-T2-D distribution.

Empirical correlations have been proposed to quantitatively relate NMR $T_2$ relaxation time of crude oils to viscosity. For example, it has been proposed that the logarithmic mean of the $T_2$ distribution ($T_{2LM}$) of crude oil shows inverse power-law dependence on viscosity ($\eta$), given as:

$$T_{2LM} = \frac{1200}{\eta^{0.9}}. \tag{1}$$

Here, $T_{2LM}$ is in milliseconds and $\eta$ is in centipoise. The correlation was modified to account for dissolved oxygen in crude oils, as shown below:

$$\eta = 9.56 \frac{T}{T_{2,LM}}, \tag{2}$$

where T is temperature in Kelvin. Other expressions relating a diffusion coefficient and viscosity also exist in literature.

Yet these techniques do not always provide accurate, dependable answers under certain conditions. Indeed, many heavy oil formations include water (in particular, clay-bound water), but the responses of heavy oil and water may overlap in the T2 domain. As such, predicting viscosity based on T2 responses may be confounded in the presence of water, such as clay-bound water. Therefore, there is a need for a method for accurate estimation of viscosity of heavy oils in the presence of water.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one aspect, the current disclosure describes a method that comprises placing a downhole tool in a wellbore in a geological formation containing heavy oil and water, obtaining nuclear magnetic resonance measurements in the wellbore, and using one or more processors to predict or identify a viscosity of the heavy oil. The nuclear magnetic resonance measurements comprise at least T1 and T2 measurements. The process of predicting or identifying the viscosity of the heavy oil may include: separating responses of the nuclear magnetic resonance measurements that are due to water from responses of the nuclear magnetic resonance measurements due to heavy oil; and relating the responses of the nuclear magnetic resonance measurements due to heavy oil to likely values of viscosity of the heavy oil based on empirical or simulated measurements.

According to some embodiments, there is disclosed a system that comprises a downhole tool configured to obtain nuclear magnetic resonance measurements in a wellbore in a geological formation containing heavy oil and water, and one or more processors that are configured to predict or identify a viscosity of the heavy oil. The nuclear magnetic resonance measurements comprise at least T1 and T2 measurements. The processors are configured to separate responses of the nuclear magnetic resonance measurements that are due to water from responses of the nuclear magnetic resonance measurements due to heavy oil. The processors are also configured to relate the responses of the nuclear magnetic resonance measurements due to heavy oil to likely values of viscosity of the heavy oil based on empirical or simulated measurements.

Also described in the current disclosure are one or more tangible, non-transitory, machine-readable media comprising instructions to receive nuclear magnetic resonance measurements obtained in a wellbore in a geological formation containing heavy oil and water, and predict or identify a viscosity of the heavy oil. The nuclear magnetic resonance measurements comprise at least T1 and T2 measurements. The process of predicting or identifying the viscosity of the heavy oil may include: separating responses of the nuclear magnetic resonance measurements that are due to water from responses of the nuclear magnetic resonance measurements due to heavy oil; and relating the responses of the nuclear magnetic resonance measurements due to heavy oil to likely values of viscosity of the heavy oil based on empirical or simulated measurements.

Various refinements of the features noted above may be undertaken in relation to various aspects of the present disclosure. Further features may also be incorporated in these various aspects as well. These refinements and additional features may exist individually or in any combination.

For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, certain features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

This disclosure describes systems and methods to predict viscosity of heavy oil in a geological formation, even when the geological formation also contains water such as claybound water, using a downhole nuclear magnetic resonance (NMR) tool. As mentioned above, downhole NMR tools may obtain responses include distributions of a first relaxation time T1, a second relaxation time T2, or diffusion, or a combination of these. For example, a downhole NMR tool may measure just T2 distribution, or the tool may measure a joint T1-T2 distribution or T1-T2-D distribution. Yet because the responses of a downhole NMR tool for heavy oil and water overlap in the T2 domain, many previously defined techniques for predicting viscosity based on T2 distributions may not be accurate in geological formations that contain both heavy oil and water.

Instead, the systems and methods of this disclosure may use certain properties of T1/T2 measurements to separate the responses of heavy oil and water. Having separated the responses due to heavy oil from those due to water, the responses due to heavy oil may be used to predict the viscosity of the heavy oil. For example, T1 and T2 distributions of the heavy oil may be related to oil viscosity using empirical approaches.

Figure 1:
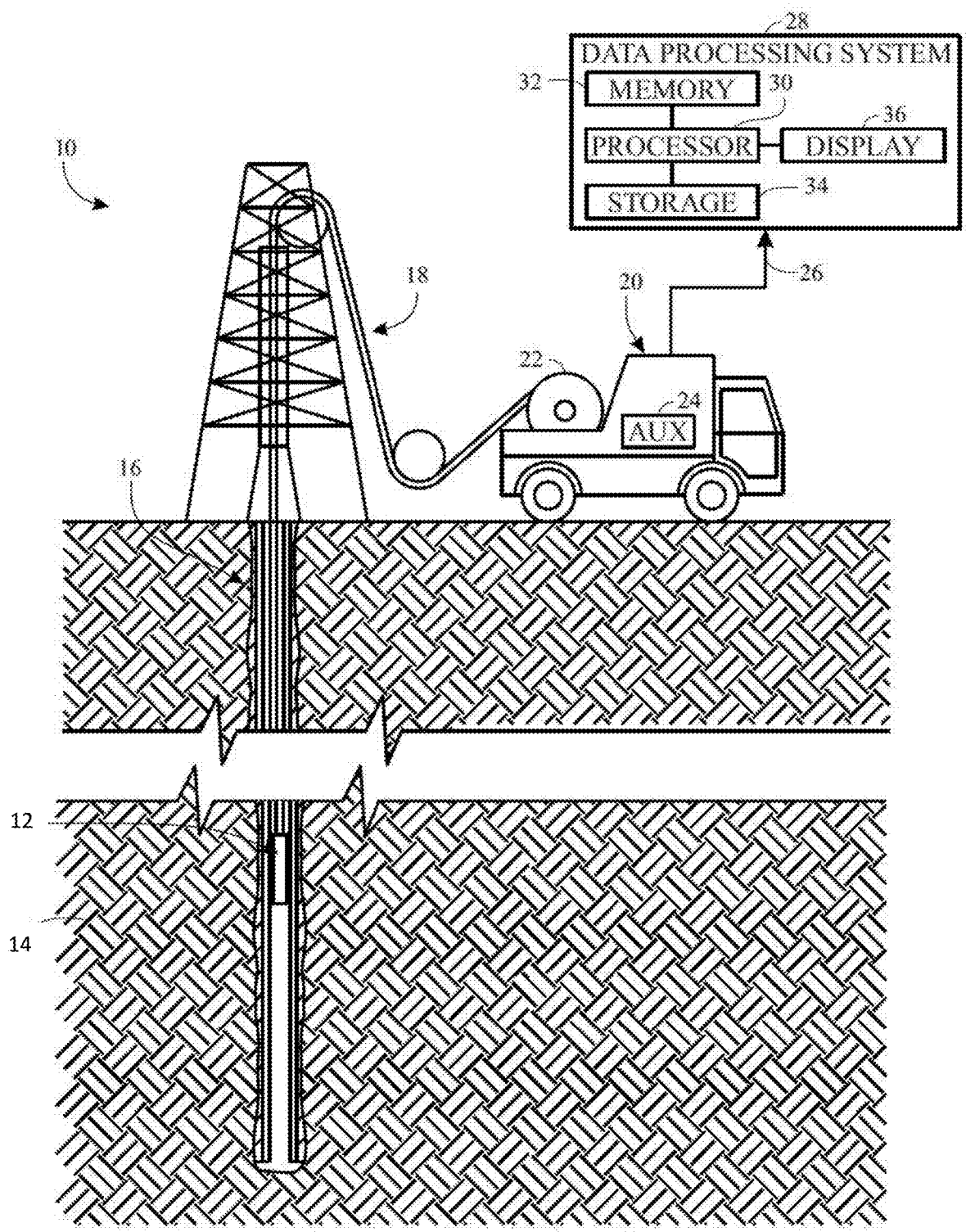
FIG. 1 is a schematic diagram of a well-logging system that may obtain nuclear magnetic resonance (NMR) logging measurements and predict or identify a viscosity of heavy oil, even in the presence of clay-bound water, in accordance with an embodiment.

With this in mind, FIG. 1 illustrates a well-logging system 10 that may employ the systems and methods of this disclosure. The well-logging system 10 may be used to convey a downhole tool 12 through a geological formation 14 via a wellbore 16. The downhole tool 12 may be conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that obtains NMR logging measurements through depths of the wellbore 16.

Many types of downhole tools may obtain NMR logging measurements in the wellbore 16. These include, for example, nuclear magnetic resonance (NMR) tools such as the Combinable Magnetic Resonance (CMR) tool, the Magnetic Resonance Scanner (MRX) tool, and the ProVISION tool by Schlumberger Technology Corporation. For each depth of the wellbore 16 that is measured, NMR tools generate NMR logging measurements that include a distribution of amplitudes of T2 relaxation time, T1 relaxation time, diffusion, or a combination thereof. This list is intended to present certain examples and is not intended to be exhaustive. Indeed, any suitable downhole tool 12 that obtains NMR logging measurements may benefit from the systems and methods of this disclosure.

The downhole tool 12 may provide such NMR logging measurements 26 to a data processing system 28 via any suitable telemetry (e.g., via electrical signals pulsed through the geological formation 14 or via mud pulse telemetry). The data processing system 28 may process the NMR logging measurements 26 to identify patterns in the NMR logging measurements 26. The patterns in the NMR logging measurements 26 may indicate certain properties of the wellbore 16 (e.g., viscosity, porosity, permeability, relative proportions of water and hydrocarbons, and so forth) that might otherwise be indiscernible by a human operator.

To this end, the data processing system 28 thus may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few examples. A display 36, which may be any suitable electronic display, may provide a visualization, a well log, or other indication of properties (e.g., viscosity of heavy oil) in the geological formation 14 or the wellbore 16 based on the NMR logging measurements 26.

Figure 2:
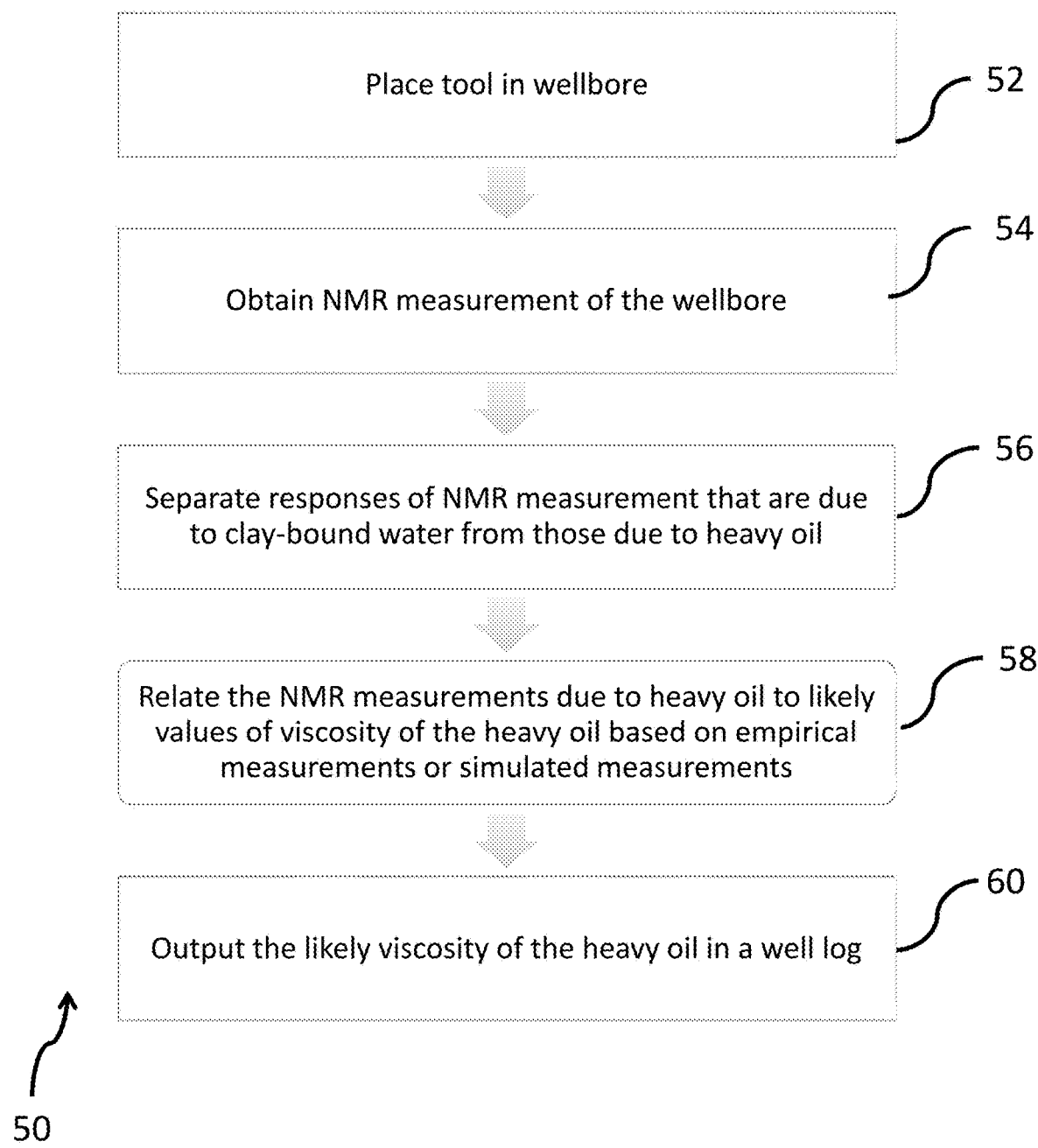
FIG. 2 is a flowchart of a method for using the system of FIG. 1, in accordance with an embodiment.

Indeed, as shown by a flowchart 50 of FIG. 2, the downhole tool 12 may be placed in the wellbore 16 (block 52) and an NMR measurement (e.g., T1 and T2 measurement) of the wellbore 16 may be obtained (block 54). The data processing system 28 may use the NMR measurement to predict likely values of viscosity of heavy oil even in the presence of water, especially the clay-bound water. First, the data processing system 28 may separate responses of the NMR measurement that are due to water from those that are due to the heavy oil (block 56). Second, the components of the NMR measurements that have been identified as due to heavy oil, rather than water, may be used to determine heavy oil viscosity. Indeed, the T1 and T2 distributions of the heavy oil may be related to a likely heavy oil viscosity using empirical approaches (e.g., relationships between T1 and T2 distributions and empirically measured values of viscosity or simulated values of viscosity) (block 58). The likely heavy oil viscosity may be output onto a well log (block 60), which may enable decisionmakers to make production and recovery decisions tailored to the viscosity conditions of the geological formation 14. The actions of blocks 56 and 58 will be discussed separately below.

Separate the Responses of the NMR Measurement that are Due to Water from Those Due to Heavy Oil (Block 56).

The NMR measurement obtained by the downhole tool 12 may have lower sensitivity to measure diffusion as the viscosity of heavy oil increases. On the other hand, it has been shown that T1 and T2 measurements can be made up to very high viscosity. For relatively low-viscosity oils, the T1 and T2 relaxation times are approximately equal, resulting in a T1/T2 ratio close to 1. Specifically, for low viscosity oils the T1 and T2 relaxation times are related to viscosity as shown below:

$$\frac{1}{T_1} = \frac{1}{T_2} \propto \frac{\eta}{T} \quad (3)$$

where $\eta$ is the viscosity of the oil in centipoise and T is temperature in Kelvin.

As the viscosity of heavy oil increases, the T1/T2 ratio deviates from unity as explained below, while the T1/T2 ratio of water remains close to 1. Therefore, the responses of heavy oil and water can be separated in the T1/T2 domain. Indeed, while NMR responses due to heavy oil may overlap in the T2 domain with responses due to water, the responses in the T1 domain may be distinct.

Figure 3:
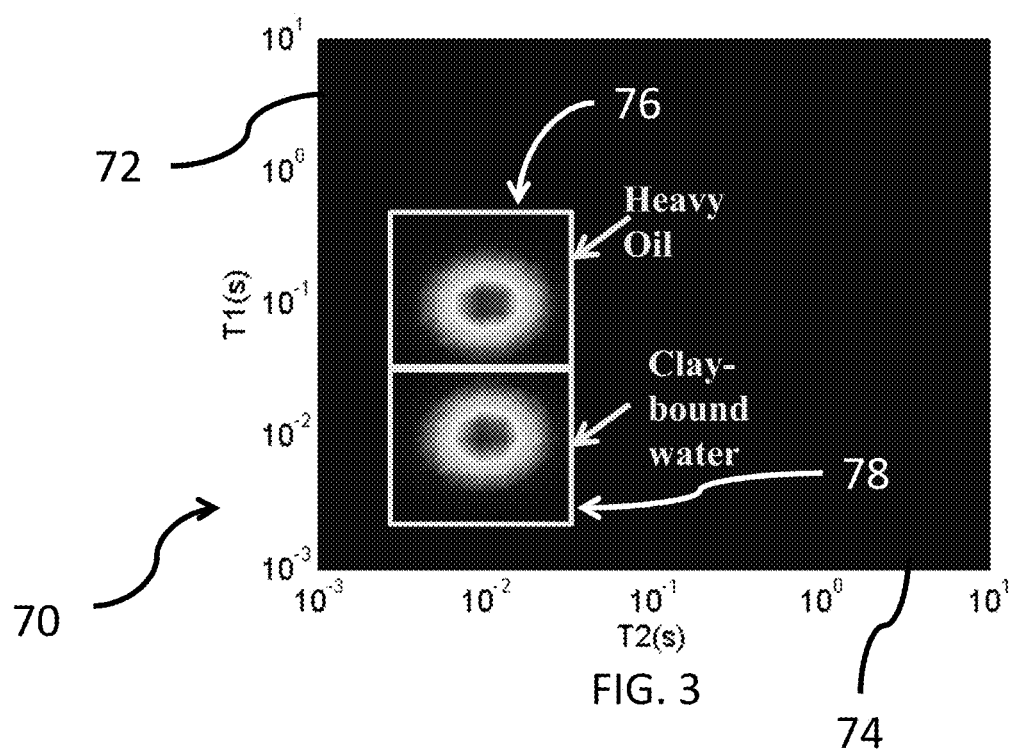
FIG. 3 is an example of a simulated T1-T2 NMR measurement in a heavy oil formation that includes water (such as clay-bound water), in accordance with an embodiment.

This is shown by example in FIG. 3, in a plot 70 of synthetic (simulated) NMR measurements from a geological formation 14 that contains both water and heavy oil of equal volumes. The plot 70 illustrates synthetic NMR measurements of T1 relaxation time (ordinate 72) and T2 relaxation time (abscissa 74). The NMR measurements appear in the plot 70 as two distinct distributions, which include a heavy-oil distribution 76 and a water distribution 78. As can be seen, the heavy-oil distribution 76 and the water distribution 78 overlap in the T2 domain, but are separate in the T1 domain. This distinction may enable the data processing system 28 to isolate the heavy-oil distribution 76 of the NMR measurements.

The data processing system 28 may use any suitable basis to distinguish between the responses from the NMR measurements due to heavy oil from those due to water, such as clay-bound water. The various NMR principles that may be used as bases to distinguish these components will be discussed briefly below. First, the relaxation mechanisms that govern longitudinal (T1) relaxation in inhomogeneous fields include intermolecular dipole-dipole coupling, intramolecular dipolar coupling, and paramagnetic relaxation. Similarly, the mechanisms that govern the transverse (T2) relaxation include intermolecular dipole-dipole coupling, intramolecular dipolar coupling, diffusion in inhomogeneous medium, and paramagnetic relaxation.

The longitudinal ($T_{1,intra}$) and transverse ($T_{2,intra}$) relaxation times due to intramolecular dipolar coupling may be given as:

$$\frac{1}{T_{1,intra}} = \frac{3\gamma^4 \hbar^2}{10 r^6} \left[ \frac{\tau}{1 + (\omega\tau)^2} + \frac{4\tau}{1 + (2\omega\tau)^2} \right] \quad (4)$$

$$\frac{1}{T_{2,intra}} = \frac{3\gamma^4 \hbar^2}{20 r^6} \left[ 3\tau + \frac{\tau}{1 + (\omega\tau)^2} + \frac{4\tau}{1 + (2\omega\tau)^2} \right] \quad (5)$$

where r is the distance between neighboring protons, $\gamma$ is the proton gyromagnetic ratio, $\hbar$ is the plank's constant, $\tau$ is the rotational correlation time and $\omega$ is the Larmor frequency. The longitudinal ($T_{1,inter}$) and transverse ($T_{2,inter}$) relaxation times due to intermolecular coupling are given by:

$$\frac{1}{T_{1,inter}} = \frac{9\gamma^4 \hbar^2}{8} [S_1(\omega) + 4S_1(2\omega)] \quad (6)$$

$$\frac{1}{T_{2,inter}} = \frac{9\gamma^4 \hbar^2}{8} \left[ \frac{3}{2} S_1(0) + \frac{5}{2} S_1(\omega) + 4S_1(2\omega) \right] \quad (7)$$

where $\gamma$, $\hbar$, $\tau$, and $\omega$ are defined above, and S1 is the Fourier spectral density function of the position of protons.

In the limit that the mean distance between protons is much larger than the atoms themselves, S1 may be expressed as:

$$S_1(\omega) = \frac{8\pi n}{45 a^3} \frac{\tau}{1 + \left(\frac{\omega\tau}{2}\right)^2} \quad (8)$$

where n is the number of protons per unit volume and a is the closest possible distance between protons.

The expressions for relaxation due to paramagnetic interactions can also be found in literature. In addition, the transverse relaxation ($T_{2,D}$) due to diffusion in an inhomogeneous field with a field gradient G is given as:

$$\frac{1}{T_{2,D}} = \frac{\gamma^2 G^2 TE^2 D}{3} \qquad (9)$$

where TE is the echo spacing and D is the diffusion coefficient. The contribution of relaxation due to diffusion can be minimized by measuring the data with relatively short echo spacing (e.g. 0.2 ms).

Figure 4:
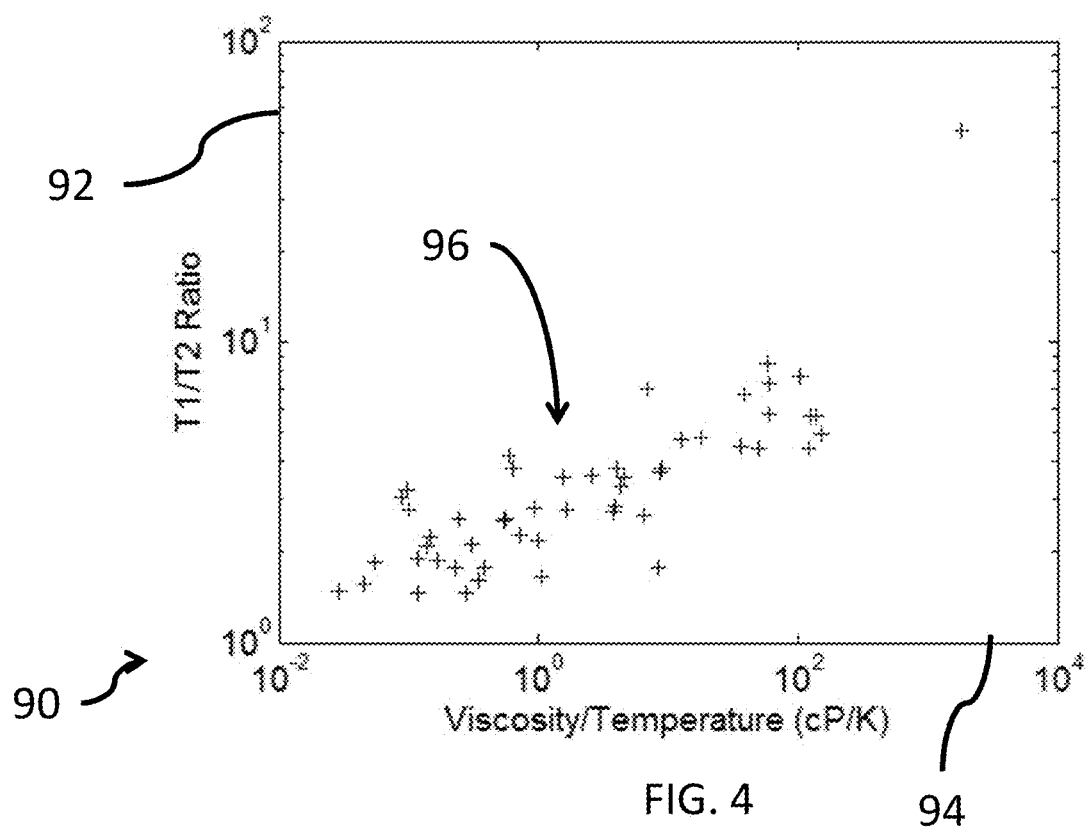
FIG. 4 is a plot that relates a T1/T2 ratio with a viscosity/temperature (cP/K) for several heavy oils, in accordance with an embodiment.

As such, considering intra and intermolecular relaxation mechanisms, the theory predicts that there may be a T1/T2 contrast greater than one for heavy oils. This is shown in a plot 90 of FIG. 4, which compares T1/T2 ratio (ordinate 92) with laboratory measurements of viscosity/temperature (cP/K) (abscissa 94). The plot 90 shows values 96 of T1/T2 ratio as a function of viscosity normalized by temperature for several heavy oils measured as measured in a laboratory setting. Consistent with the theory described by the relationships noted above, the T1/T2 ratio increases as the viscosity of the heavy oil increases. This contrast in the T1/T2 ratio can be used to distinguish a heavy oil distribution in NMR measurements of T1 and T2 from that of water. It should be noted that other metrics based on the T1 and T2 relaxation mechanisms can also be used, such as T1/T2 distributions and difference in T2 and T1 relaxation rates, called secular relaxation rate ($T_{2,sec}$), and defined below:

$$\frac{1}{T_{2,sec}} = \frac{1}{T_2} - \frac{1}{T_1} \qquad (10)$$

There are several methods for identification of heavy oil and water response from T1-T2 measurements. In one example, the T1-T2 maps could be partitioned into oil and water responses by applying suitable cutoffs. In some other embodiments, the method for identifying oil and water responses is based on the use of data analytics approach as described in the co-pending, co-assigned U.S. patent application with Ser. No. 62/249,257, the entire contents of which are incorporated by reference into the current application. In simple terms, the NMR data obtained from a wellbore can be arranged in a matrix and decomposed as a product of two non-negative "component" matrices. The first component matrix may contain the response of different fluids and the second component matrix may contain the relative proportions (e.g. volumetric fractions) of the fluids for each measurement. Other decomposition methods can also be used to differentiate heavy oil responses from water response based on T1-T2 measurements.

Thus, the data processing circuitry 28 may use one or more of these or any other suitable principles of T1/T2 contrast to distinguish between those components of the NMR measurement due to heavy oil and those due to water. Relate the NMR Measurements Due to Heavy Oil to Likely Values of Viscosity of the Heavy Oil Based on Empirical or Simulated Measurements (Block 58).

Having identified the components of the NMR measurements due to heavy oil from those of water, the data processing system 28 may use the components of the NMR measurement due to heavy oil to predict likely values of viscosity of the heavy oil. The estimation of heavy oil viscosity from the T1 and T2 measurements can be done using empirical and/or simulated correlations. Moreover, the parameters could be customized for each type of tool, or even each individual tool, that has been used to obtain the NMR measurements. Additionally or alternatively, the T1 and T2 measurements may be mapped to the oil viscosity using a non-linear function mapping using a database of laboratory measurements and/or simulated measurements. In one example, the mapping function is a linear combination of Gaussian Radial Basis Functions (RBFs) as shown below:

$$\log(\eta) = \frac{\sum_{j=1}^{N} c_j \exp\left(-\frac{\|A_T - A_{T,j}\|^2}{2s_j^2}\right)}{\sum_{j=1}^{N} \exp\left(-\frac{\|A_T - A_{T,j}\|^2}{2s_j^2}\right)} \qquad (11)$$

where N is the number of heavy oil samples in the database and $\vec{A}_T$ is given by:

$$\vec{A}_T = \vec{A}_T(A(T_1), A(T_2), T) \qquad (12)$$

where η is the viscosity of the oil in centipoise, T is temperature in Kelvin, and s is the widths of the Gaussian RBFs.

Figure 5:
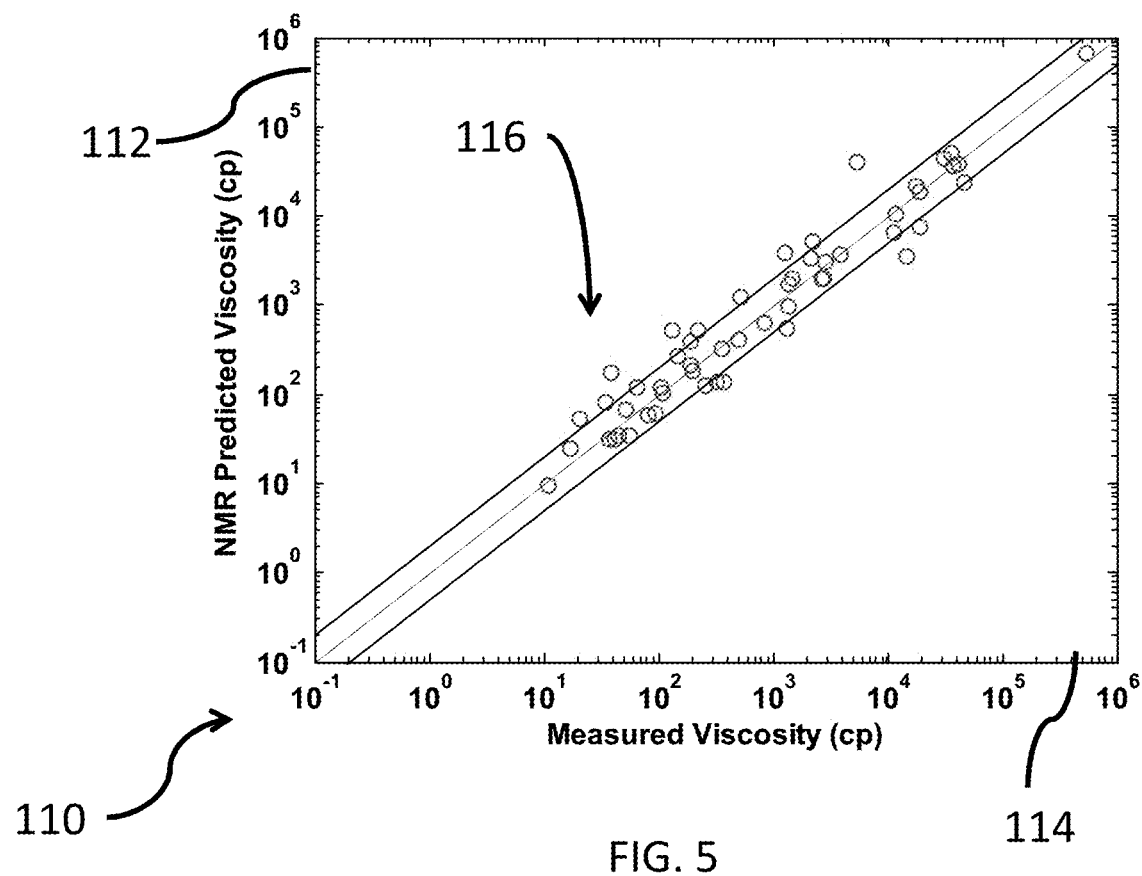
FIG. 5 is a plot that compares a predicted viscosity as predicted using NMR measurements in accordance with this disclosure and measured viscosity as empirically measured, in accordance with an embodiment.

An interpolation function can be constructed using the logarithm of viscosity, which may be more accurate in some respects, and which has a smaller dynamic range. An example plot 110 shown in FIG. 5 compares estimated viscosity in units of cp (ordinate 112) that has been predicted in accordance with the systems and methods of this disclosure with laboratory-measured viscosity in units of cp (abscissa 114). Even with a variety of different samples 116 of heavy oils, the technique of this disclosure produces estimated viscosity results that accurately align with measured viscosity values. In the particular example shown in FIG. 5, the viscosity values are estimated using modified radial basis function interpolation as described above and using the amplitudes of $T_2$ and $T_1$ distribution in the input vector. The viscosities are estimated within a logarithmic standard deviation of 1.53.

Figure 6:
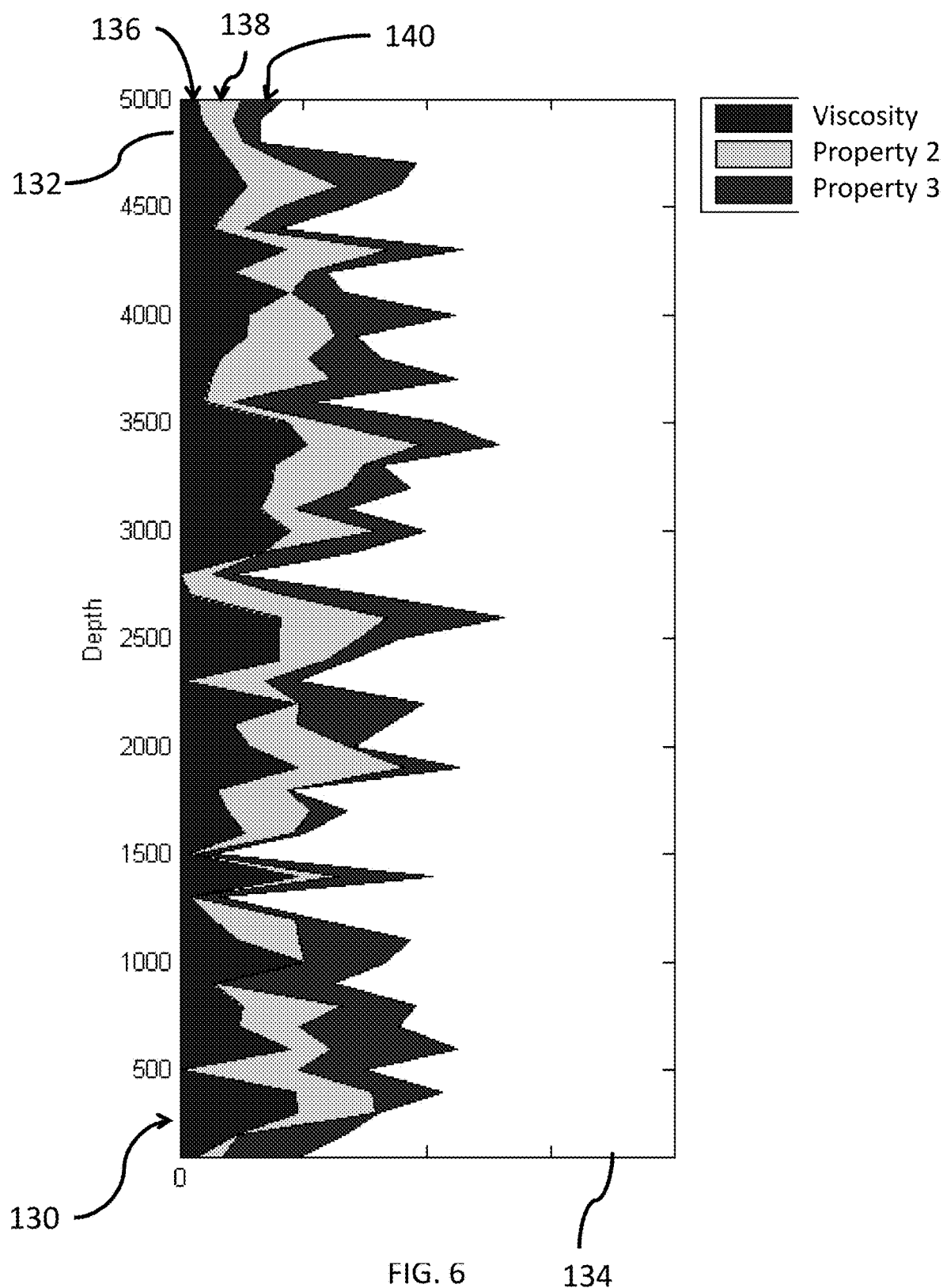
FIG. 6 is a well log representing a visualization of the predicted viscosity of heavy oil in a heavy oil formation that also includes water, in accordance with an embodiment.

The values of oil viscosity may be presented in any suitable manner. In one example, the viscosity may be presented alongside other features in a visualization such as a well log 130 shown in FIG. 6. The well log 130 represents changes over depth (ordinate 132) in well property values (abscissa 134). These may include viscosity 136 and two other features 138 and 140 (e.g., density, porosity, and so forth). By presenting the identified underlying features in a visualization of viscosity such as this, a human operator may be able to effectively make decisions relating to the management and/or operation of the well.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

The invention claimed is:
1. A method comprising:
   placing a downhole tool in a wellbore in a geological formation containing heavy oil and water;

obtaining nuclear magnetic resonance measurements in the wellbore, wherein the nuclear magnetic resonance measurements comprise at least T1 and T2 measurements;

using one or more processors to determine a viscosity of the heavy oil including by:

separating responses of the nuclear magnetic resonance measurements that are due to water from responses of the nuclear magnetic resonance measurements due to heavy oil by:

(1) arranging the nuclear magnetic resonance measurements in a matrix and decomposing the matrix as a product of a first component matrix and a second component matrix, wherein the first component matrix comprises vectors that describe various fluids in the geological formation and the second component matrix comprises corresponding proportions of the fluids in the geological formation; or (2) partitioning a plot of T1 and T2 measurements into sections attributable to water and sections attributable to heavy oil; or (3) determining a secular relaxation rate ($T_{2,sec}$) as defined below:

$$\frac{1}{T_{2,sec}} = \frac{1}{T_2} - \frac{1}{T_1};$$

and relating the responses of the nuclear magnetic resonance measurements due to heavy oil to values of viscosity of the heavy oil based on empirical or simulated measurements.

2. The method of claim 1, wherein separating the responses of the nuclear magnetic resonance measurements that are due to water from the responses of the nuclear magnetic resonance measurements due to heavy oil comprises identifying a contrast between a first distribution and a second distribution in a T1 domain.

3. The method of claim 1, wherein relating the responses of the nuclear magnetic resonance measurements due to heavy oil to values of viscosity of the heavy oil comprises mapping the T1 and T2 measurements to the viscosity of the heavy oil using a non-linear function mapping using a database of laboratory measurements, simulated measurements, or both.

4. The method of claim 3, wherein mapping function is a linear combination of Gaussian Radial Basis Functions (RBFs) as shown below:

$$\log(\eta) = \frac{\sum_{j=1}^{N} c_j \exp\left(-\frac{\|A_T - A_{T,j}\|^2}{2s_j^2}\right)}{\sum_{j=1}^{N} \exp\left(-\frac{\|A_T - A_{T,j}\|^2}{2s_j^2}\right)}$$

where N is the number of heavy oil samples in the database and $\vec{A}_T$ is given by:

$$\vec{A}_T = \vec{A}_T(A(T_1), A(T_2), T)$$

where $\eta$ is the viscosity of the oil in centipoise, T is temperature in Kelvin, and s is the widths of the Gaussian RBFs.

5. The method of claim 1, further comprising constructing an interpolation function using a logarithm of the viscosity of the heavy oil.

6. The method of claim 1, further comprising displaying the separated responses of heavy oil and water on a log.

7. A system comprising:

a downhole tool configured to obtain nuclear magnetic resonance measurements in a wellbore in a geological formation containing heavy oil and water, wherein the nuclear magnetic resonance measurements comprise at least T1 and T2 measurements;

one or more processors configured to determine a viscosity of the heavy oil including by:

separating responses of the nuclear magnetic resonance measurements that are due to water from responses of the nuclear magnetic resonance measurements due to heavy oil; and relating the responses of the nuclear magnetic resonance measurements due to heavy oil to values of viscosity of the heavy oil based on empirical or simulated measurements by mapping the T1 and T2 measurements to the viscosity of the heavy oil using a non-linear function mapping using a database of laboratory measurements, simulated measurements, or both, wherein mapping function is a linear combination of Gaussian Radial Basis Functions (RBFs) as shown below:

$$\log(\eta) = \frac{\sum_{j=1}^{N} c_j \exp\left(-\frac{\|A_T - A_{T,j}\|^2}{2s_j^2}\right)}{\sum_{j=1}^{N} \exp\left(-\frac{\|A_T - A_{T,j}\|^2}{2s_j^2}\right)}$$

where N is the number of heavy oil samples in the database and $\vec{A}_T$ is given by:

$$\vec{A}_T = \vec{A}_T(A(T_1), A(T_2), T)$$

where $\eta$ is the viscosity of the oil in centipoise, T is temperature in Kelvin, and s is the widths of the Gaussian RBFs.

8. The system of claim 7, wherein separating the responses of the nuclear magnetic resonance measurements that are due to water from the responses of the nuclear magnetic resonance measurements due to heavy oil comprises identifying a contrast between a first distribution and a second distribution in a T1 domain.

9. The system of claim 7, wherein separating the responses of the nuclear magnetic resonance measurements that are due to water from the responses of the nuclear magnetic resonance measurements due to heavy oil comprises arranging the nuclear magnetic resonance measurements in a matrix and decomposing the matrix as a product of a first component matrix and a second component matrix, wherein the first component matrix comprises vectors that describe various fluids in the geological formation and the second component matrix comprises corresponding proportions of the fluids in the geological formation.

10. The system of claim 7, wherein separating the responses of the nuclear magnetic resonance measurements that are due to water from the responses of the nuclear magnetic resonance measurements due to heavy oil comprises partitioning a plot of T1 and T2 measurements into sections attributable to water and sections attributable to heavy oil.

11. The system of claim 7, wherein separating the responses of the nuclear magnetic resonance measurements that are due to water from the responses of the nuclear magnetic resonance measurements due to heavy oil comprises determining a secular relaxation rate ($T_{2,sec}$) as defined below:

$$\frac{1}{T_{2,sec}} = \frac{1}{T_2} - \frac{1}{T_1}.$$

12. The system of claim 7, wherein the one or more processors are further configured to construct an interpolation function using a logarithm of the viscosity of the heavy oil.

13. The system of claim 7, wherein the one or more processors are further configured to display the separated responses of heavy oil and water on a log.

14. One or more tangible, non-transitory, machine-readable media comprising instructions that, when executed by at least one processor, cause the at least one processor to perform a method, the method comprising:
   receiving nuclear magnetic resonance measurements obtained in a wellbore in a geological formation containing heavy oil and water, wherein the nuclear magnetic resonance measurements comprise at least T1 and T2 measurements;
   determining a viscosity of the heavy oil including by:
      separating responses of the nuclear magnetic resonance measurements that are due to water from responses of the nuclear magnetic resonance measurements due to heavy oil by:
         (1) arranging the nuclear magnetic resonance measurements in a matrix and decomposing the matrix as a product of a first component matrix and a second component matrix, wherein the first component matrix comprises vectors that describe various fluids in the geological formation and the second component matrix comprises corresponding proportions of the fluids in the geological formation; or
         (2) partitioning a plot of T1 and T2 measurements into sections attributable to water and sections attributable to heavy oil; or
         (3) determining a secular relaxation rate ($T_{2,sec}$) as defined below:

$$\frac{1}{T_{2,sec}} = \frac{1}{T_2} - \frac{1}{T_1};$$

and
      relating the responses of the nuclear magnetic resonance measurements due to heavy oil to values of viscosity of the heavy oil based on empirical or simulated measurements.

15. The media of claim 14, wherein relating the responses of the nuclear magnetic resonance measurements due to heavy oil to values of viscosity of the heavy oil comprises mapping the T1 and T2 measurements to the viscosity of the heavy oil using a non-linear function mapping using a database of laboratory measurements, simulated measurements, or both.

* * * * *